United States Patent [19] [11] Patent Number: 4,846,936
Tsurumaru et al. [45] Date of Patent: Jul. 11, 1989

[54] METHOD AND APPARATUS FOR MEASURING METAL EXPOSURE IN RESIN COVERING PORTION IN METAL CONTAINER AND CONSTITUENT MEMBER THEREOF

[75] Inventors: Michiko Tsurumaru, Tokyo; Yukio Suzuki, Kawasaki; Fumihiro Tsutsumi, Tokyo; Masato Ashina, Yokosuka; Hironori Kobayashi, Chofu, all of Japan

[73] Assignee: Toyo Seikan Kaisha, Ltd., Tokyo, Japan

[21] Appl. No.: 84,363

[22] Filed: Aug. 12, 1987

[30] Foreign Application Priority Data

Aug. 12, 1986 [JP] Japan .................... 61-187900

[51] Int. Cl.$^4$ ............................ G01N 27/24
[52] U.S. Cl. .................... 204/1 T; 204/406; 204/434; 324/71.1; 324/514; 324/515; 324/558; 324/559
[58] Field of Search ........... 204/1 T, 434, 400, 406; 324/425, 71.1, 515, 558, 559, 514

[56] References Cited

U.S. PATENT DOCUMENTS 3,106,677 10/1963 Edgar .................... 324/559
3,210,655 10/1965 McGlasson et al. ........ 324/559
4,332,646 6/1982 Tsurumaru et al. ........ 204/1 T

FOREIGN PATENT DOCUMENTS 239665 11/1985 Japan .................... 324/71.1

OTHER PUBLICATIONS

James A. Plambeck, "Electroanalytical Chemistry", pp. 27, 28, (1982).

Primary Examiner—G. L. Kaplan
Attorney, Agent, or Firm—Sughrue, Mion, Zinn, Macpeak, and Seas

[57] ABSTRACT

Disclosed is a method for measuring the metal exposure in a resin covering area of a metal container or a constituent member thereof, which comprises contacting the resin covering area of the metal container or the constituent member thereof with a measuring electrode through an electrolytic solution, relatively moving the resin covering area and the measuring electrode in a certain direction while always holding the electrolytic solution between the measuring electrode and the resin covering area, measuring a leak current between the metal substrate of the metal container or constituent member at predetermined pitches and detecting the metal exposure of the resin covering area as leak currents at respective parts discriminately.

According to this measuring method, the degree of the metal exposure can be easily measured as the leak current at respective parts discriminately, and statistical processing of the measured leak current values can be easily performed.

8 Claims, 8 Drawing Sheets

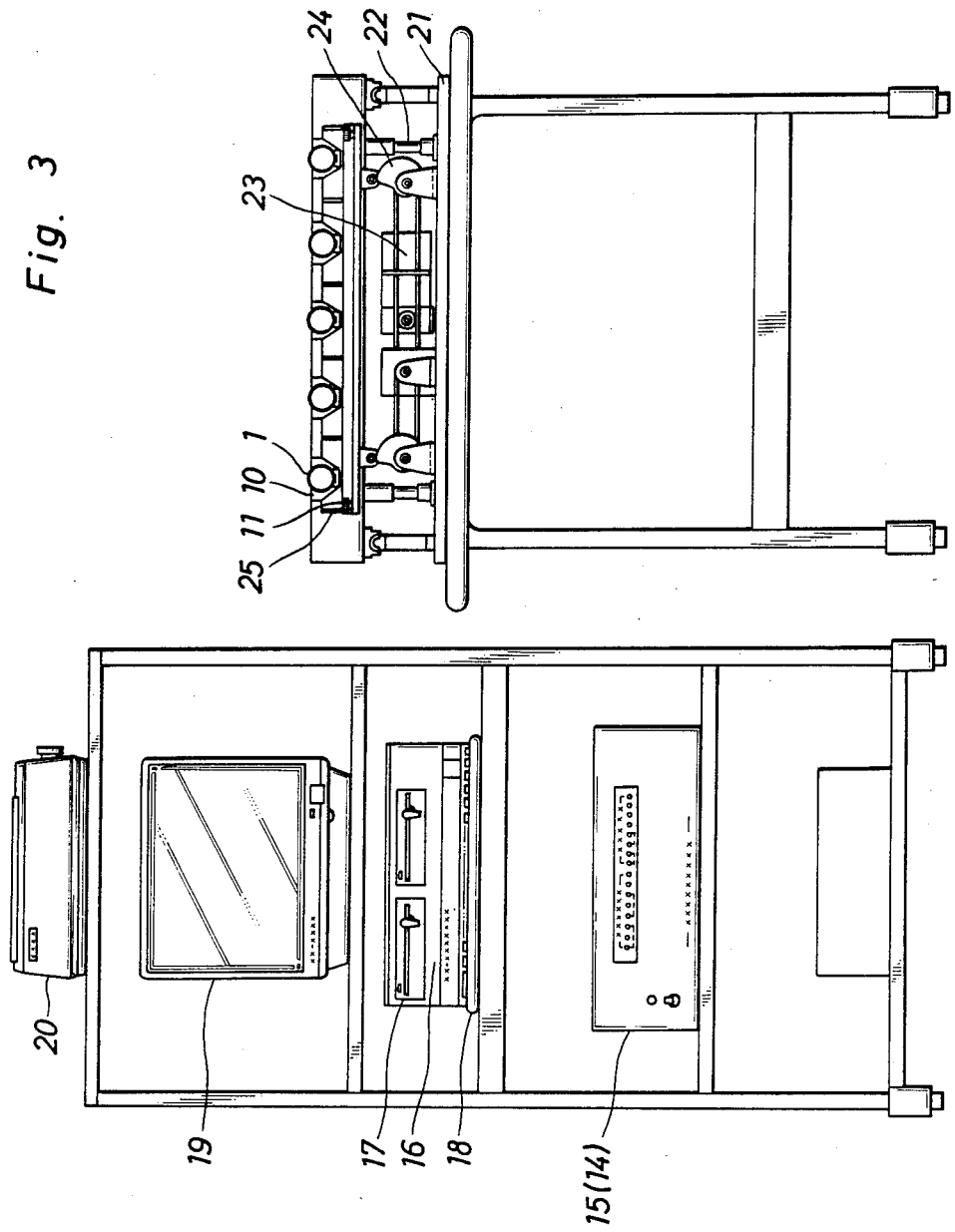

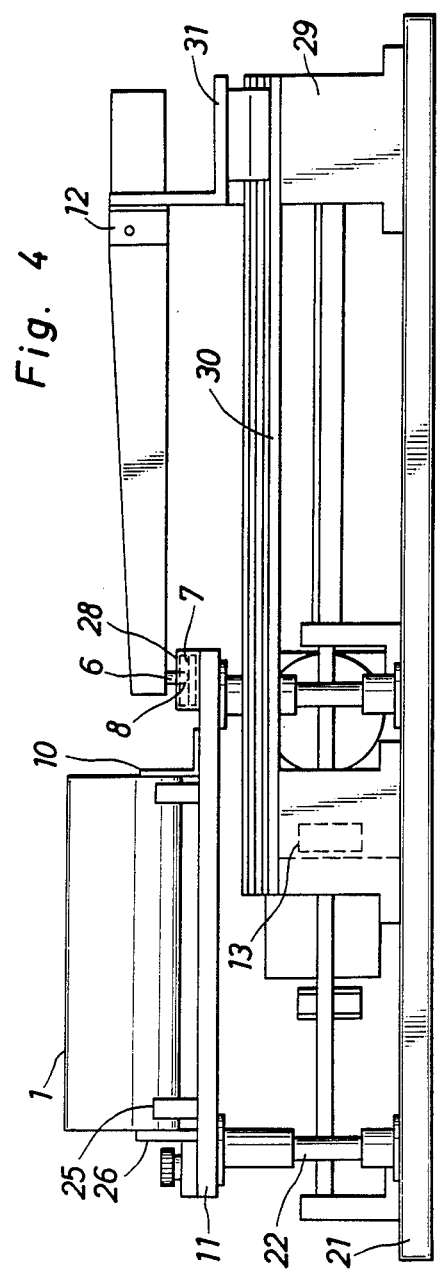
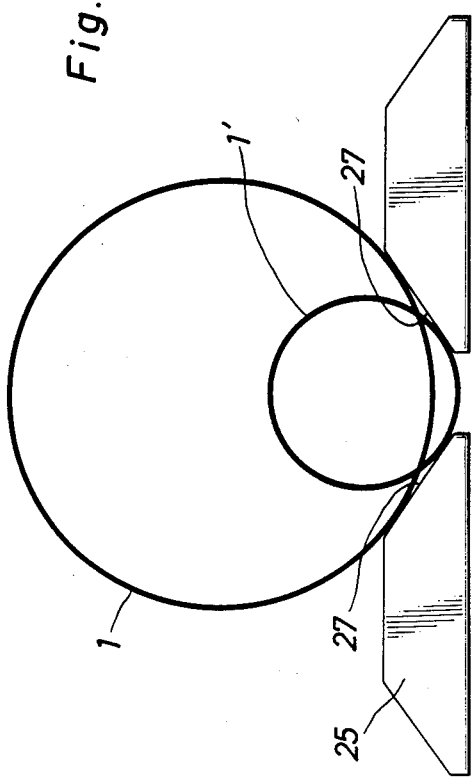

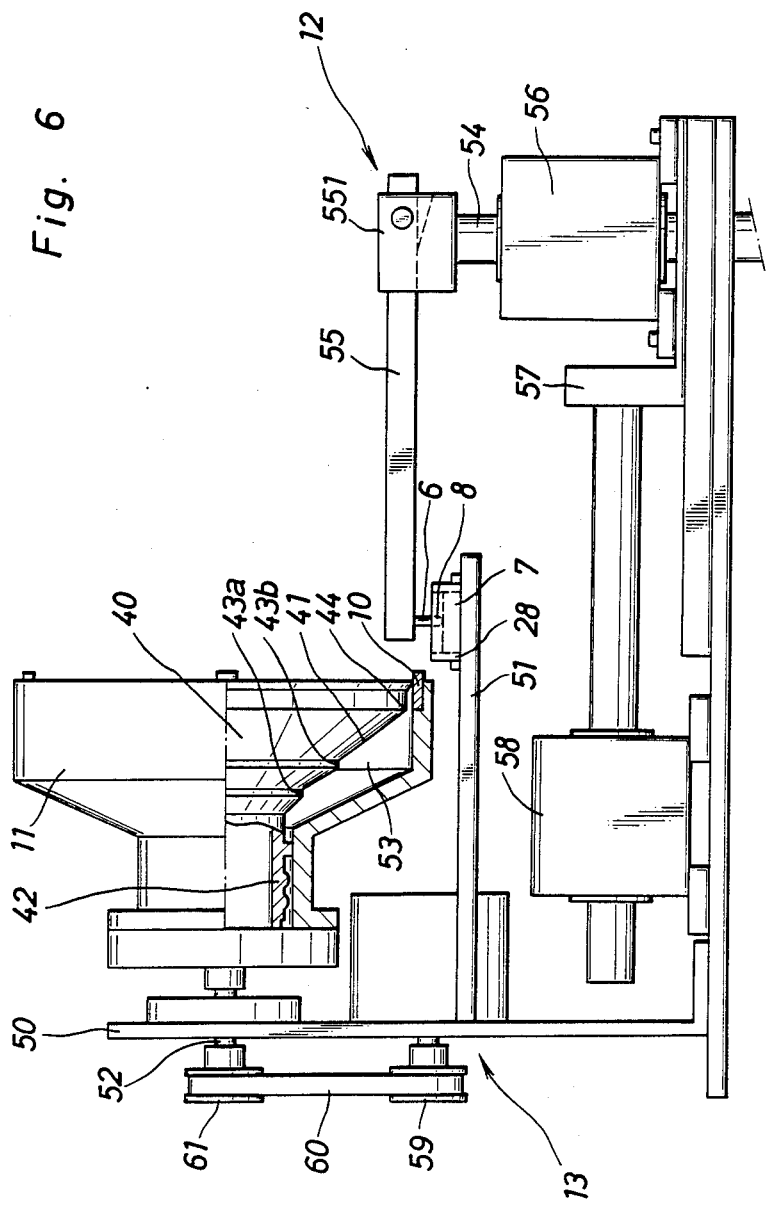

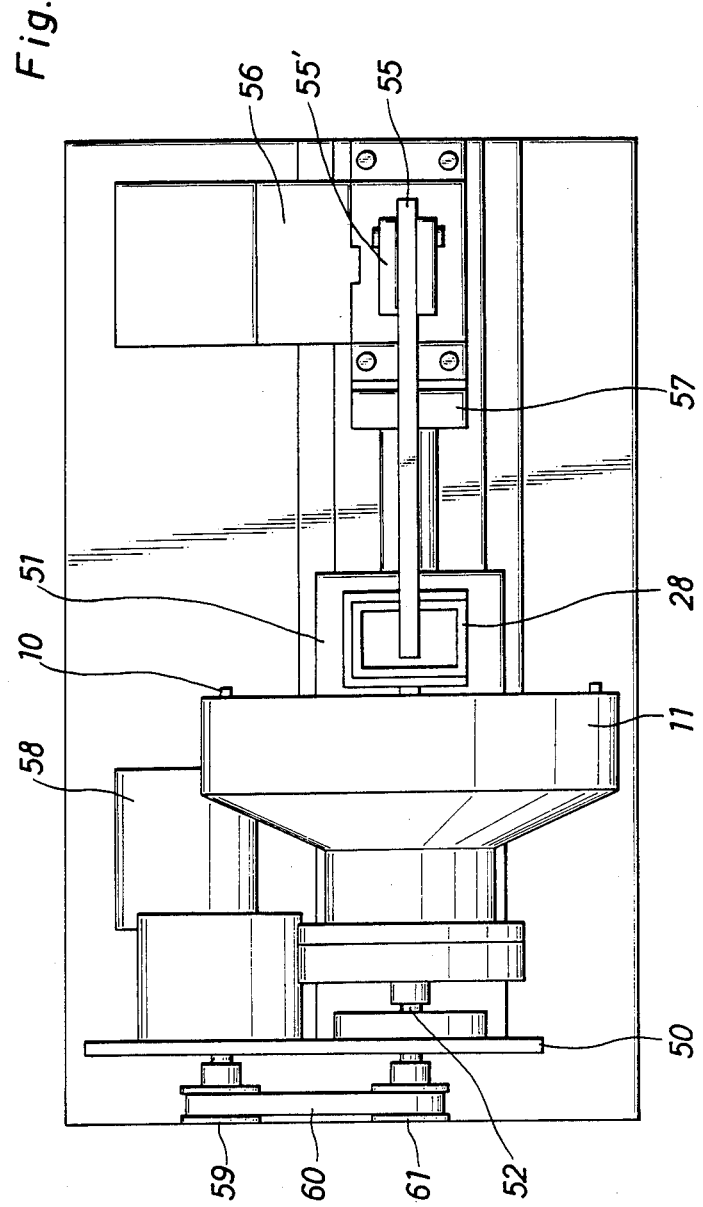

METHOD AND APPARATUS FOR MEASURING METAL EXPOSURE IN RESIN COVERING PORTION IN METAL CONTAINER AND CONSTITUENT MEMBER THEREOF

BACKGROUND OF THE INVENTION (1) Field of the Invention

The present invention relates to a method and an apparatus for measuring the metal exposure in a resin covering area of a metal container or a constituent member thereof. More particularly, the present invention relates to a measurement method and an apparatus in which the metal exposure in a seam, a fabricated area, a lap-seamed area or a bonded area of a metal container or a constituent member thereof such as a can body or a can lid can be detected with respect to fine parts discriminately.

(2) Description of the Prior Art

In the field of metal containers, at least the inner surface of a container is ordinarly covered with an organic resin lacquer so as to prevent dissolution of a metal into a content and corrosion of the metal. For this purpose, a metal blank coated with an organic resin is used in the production of a body or lid of a container, a stripe coating is applied in a side seam formed by welding or the like, and repair coating is applied on a scored area or riveted area of a can lid or a side-seamed area or bonded area between a lid and a body by spraying an organic resin lacquer.

As means for evaluating the metal exposure in a resin covering area in a metal container or a contituent member thereof, there is known the so-called enamel rater test. At this enamel rater test, an electrolytic aqueous solution is filled in a container or the like, a measuring electrode is immersed in this electrolytic solution, a voltage is applied between this electrode and the metal of the container, and the degree of the metal exposure is detected as a leak current between them.

At the above-mentioned enamel rater test, however, only the entire metal exposure of the container or the constituent member thereof is determined as an integrated value of the leak current, and it is difficult to evaluate the degree of the metal exposure at respective parts of the resin covering area discriminately.

The defect of the metal exposure in the resin coated area of a metal container or a constituent member thereof tends to appear at specific parts relatively to a processing tool or a processing operation. It is obvious that if the degree of the metal exposure is precisely evaluated at respective parts, the exposure of the metal can be prevented and the problem of dissolution of the metal or corrosion of the metal container can be solved by modifying a processing tool or improving a processing operation.

SUMMARY OF THE INVENTION

It is therefore a primary object of the present invention to overcome the defect of the conventional enamel rater test and provide a method and an apparatus in which the degree of the metal exposure can be simply measured as a leak current at respective parts discriminately.

In accordance with one fundamental aspect of the present invention, there is provided a method for measuring the metal exposure in a resin covering area of a metal container or a constituent member thereof, which comprises contacting the resin covering area of the metal container or the constituent member thereof with a measuring electrode through an electrolytic solution, relatively moving the resin covering area and the measuring electrode in a certain direction while always holding the electrolytic solution between the measuring electrode and the resin covering area, measuring a leak current between the metal substrate of the metal container or constituent member and the measuring electrode at predetermined pitches and detecting the metal exposure of the resin covering area as leak currents at respective parts discriminately.

In accordance with another aspect of the present invention, there is provided an apparatus for measuring the metal exposure in a resin covering area of a metal container or a constituent member thereof, which comprises a supporting member for supporting the metal container or the constituent member thereof having the resin covering area in the state electrically conductive to a contact electrode, an electrode supporting mechanism including a measuring electrode and an electrolytic solution-holding member mounted on the tip of the measuring electrode, said electrode supporting mechanism being arranged so that the resin covering area of the metal container or the constituent member thereof is contacted with the measuring electrode through the electrolytic solution, a driving mechanism for relatively moving said supporting member and said electrode supporting mechanism while keeping said contact state, a drive control mechanism for controlling the driving of said driving mechanism according to predetermined parts to be measured, an interface zone for applying a voltage between the contact electrode and the measuring electrode, measuring a leak current at every pitch of said relatively movement and performing analog-digital conversion of the measured current value, and a data processing zone for performing statistical processing of the digital-converted data and displaying or recording the obtained data.

BRIEF DESCRIPTION OF THE DRAWINGS

FIG. 3 is a diagram illustrating a systematic arrangement of the apparatus for use in carrying out the measurement method of the present invention.

FIG. 4 is a side view illustrating a main part of the apparatus used for measuring the metal exposure of a straight side seam.

FIG. 5 is a sectional view showing a holder of the apparatus shown in FIG. 4.

FIG. 6 is a side view illustrating a main part of the apparatus used for measuring the metal exposure in a circumferential processed area of a cup-shaped lid.

FIG. 7 is a top view of the apparatus shown in FIG. 6.

Figure 1:
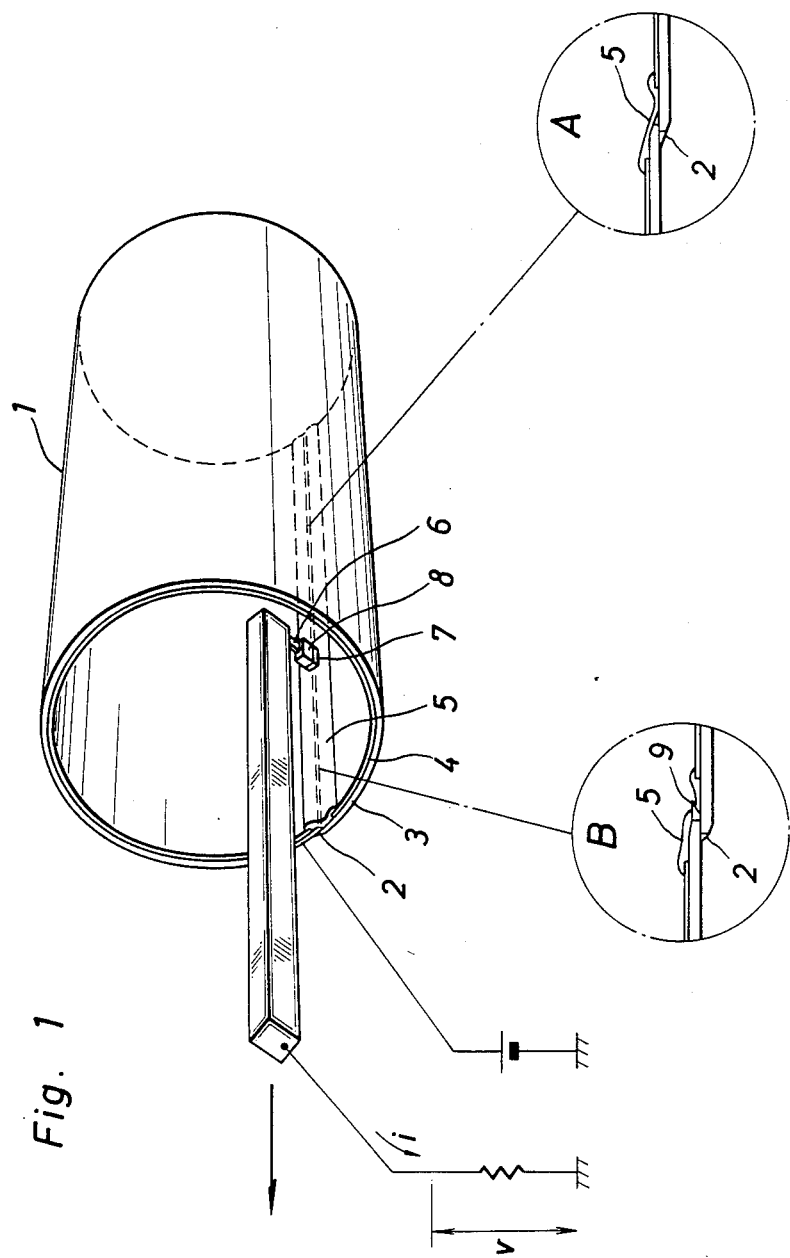
FIG. 1 is a diagram illustrating the principle of the method for measuring the metal exposure according to the present invention.

In the drawings, each of reference numerals 1, 40 and 70 represents a sample to be measured, reference numeral 2 represents a seam, reference numeral 3 represents a metal blank, reference numeral 4 represents an inner surface protecting coating, reference numeral 5 represents a reparing resin covering layer, reference numeral 6 represents a measuring electrode, reference numeral 7 represents an electrolytic solution, reference numeral 8 represents an electrolytic solution holding member, reference numeral 9 represents a metal-exposed part, reference numeral 10 represents a contact electrode, reference numeral 11 represents a sample supporting member, reference numeral 12 represents an electrode supporting mechanism, reference numeral 13 represents a driving mechanism, reference numeral 14 represents a drive control mechanism, reference numeral 15 represents an interface zone, reference numeral 16 represents a data processing zone, reference numeral 17 represents a computer, reference numeral 18 represents a keyboard, reference numeral 19 represents CRT, and reference numeral 20 represents a printer.

DETAILED DESCRIPTION OF THE PREFERRED EMBODIMENTS

Referring to FIG. 1 illustrating the principle of the present invention, a metal can 1 as the sample to be measured has a seam 2 formed by welding, and in the area other than the seam, an inner surface protecting coating 4 is formed on the inner surface of a metal blank 3 and a repairing resin covering layer 5 is formed on the weld seam 2.

A measuring electrode 6 used in the present invention generally has on the tip thereof a holding member 8 for holding an electrolytic solution 7, and the measuring electrode 6 is electrically contacted with the reparing resin covering layer 5 of the metal can 1 through the electrolytic solution 7.

Referring to FIG. 1, the weld seam 2 is completely covered with the reparing resin covering layer 5 at a measurement position A and no metal-exposed part is present. On the other hand, at a measurement position B, there is present a metal-exposed part because of irregular protrusion of a molten metal on the weld seam 2 at the welding step or insufficient wetting with the covering resin on the weld seam 2.

According to the present invention, the measuring electrode 6 and the metal can 1 are relatively moved in a certain direction along the weld seam 2. During this movement, the electrical contact state is always maintained between the measuring electrode 6 and the reparing resin covering layer 5 through the electrolytic solution 7, and at every certain pitch (distance) of the relative movement, a measurement voltage is applied between the metal blank 3 and the electrode 6 and a leak current between them is measured. When the electrode 6 is located at the measurement position A, since the seam 2 is completely covered with the reparing resin covering layer 5, no leak current is detected. When the electrode 6 arrives at the measurement position B, the conductive state is produced between the metal-exposed part 9 and the electrode 6 through the electrolytic solution 7 and a leak current is detected. Since the amplitude of the leak current generated between the metal-exposed part 9 and the electrode 6 is proportional to the area of the metal-exposed part 9, the degree of the metal exposure at the metal-exposed part can be known from the amplitude of the leak current at every pitch, and if leak currents at respective pitches are determined, the positions of the metal-exposed parts and the distribution thereof can be precisely determined.

Figure 2:
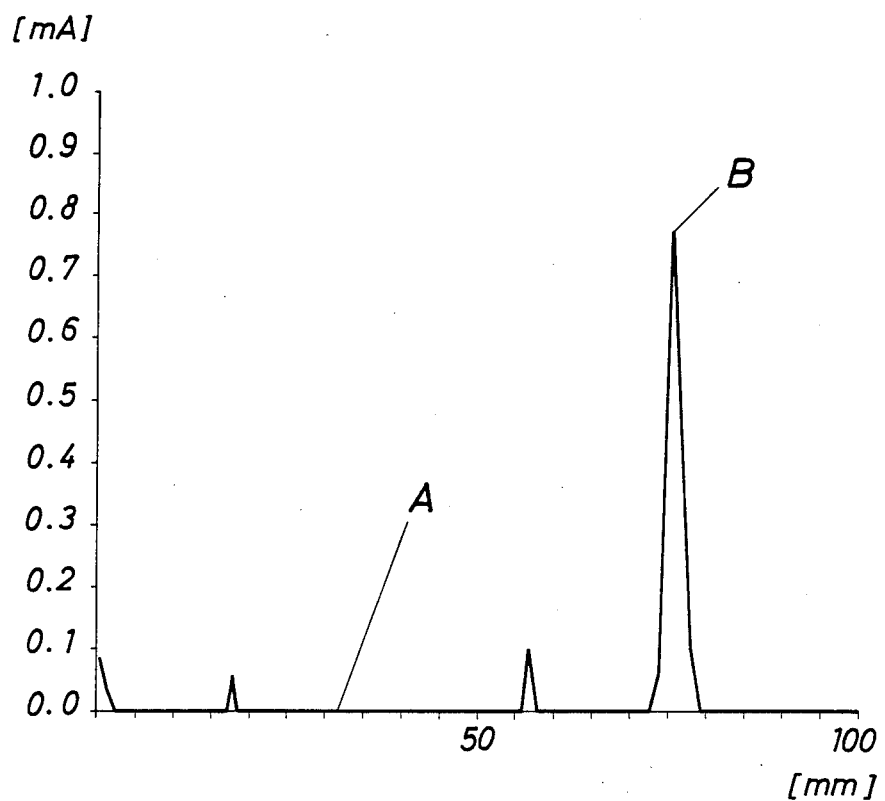
FIG. 2 is a graph illustrating an example of the relation between the distance in the height direction of the seam and the leak current in a seam-covered welded can.

FIG. 2 of the accompanying drawings illustrates the relation between the distance of the seam in the height direction of the can and the leak current, determined practically with respect to a seam-covered welded can, and from FIG. 2, it will be readily understood that the degree of the metal exposure in the resin-covered area can be detected at respective positions discriminately.

It is important that at the relative movement of the measuring electrode 6 and the sample 1 to be measured, the electrolytic solution 7 should be disposed between the measuring electrode 6 and the resin covering 5. It was found that when mercury is used instead of the electrolytic solution, it is difficult to detect fine metal-exposed parts. It is considered that the reason is that although mercury is excellent in the electroconductivity, since the surface tension is large, it is difficult for mercury to intrude into a fine resin-free part and wet a metal-exposed part.

In the present invention, in view of the precision of the measurement of the leak current, it is preferred that the electrolytic solution 7 be held in the form of liquid drops or small masses between the measuring electrode 6 and the resin covering 5 and a continuous film of the electrolytic solution be not left on the resin covering 5 after the measuring electrode 6 has passed. This can be accomplished by selecting the material or porous structure of the holding member 8 to appropriately adjust the retention quantity of the electrolytic solution or by controlling the characteristics of the electrolytic solution, such as the surface tension or the covering-wetting property. However, in the present invention, it should be understood that even if certain trailing of the liquid is caused on the surface of the resin covering after the measuring electrode 6 has passed, the metal-exposed part can be measured at every certain pitch with a considerably high precision. The reason is that although the distance between the measuring electrode 6 and the metal-exposed part 9 is generally 0.1 $\mu$m to 5 mm when the measuring electrode 6 is located just above the metal-exposed part 9, the measurement pitch is about 0.1 to 10 mm, and the measured value of the leak current is inversely proportional to the resistance value between the measuring electrode 6 and the metal-exposed part 9, that is, the length of the electrolytic solution in the scanning direction. Accordingly, if a distance larger than the measurement pitch is present between adjacent metal-exposed parts, since the value of the leak current of the metal-exposed part to be now measured is much larger than the measured value of the leak current of the already measured metal-exposed part, both the values can be distinguished from each other.

The method for measuring the metal exposure can be widely applied to the measurement of the metal exposure in resin covering areas of metal containers or constituent members thereof. In the case where the area to be measured is a straight covering area as in the above-mentioned covered welded can, it is sufficient if the relative movement is performed so that the measuring electrode traces the straight covering area. In case of a container having a circumferential seam, it is sufficient if the container is rotated and the leak current is measured with respect to the covered area along the circumferential seam by the measuring electrode. In case of an easy-opening lid having a scored area or riveted area, it is sufficient if the measuring electrode traces such a fabricated area. Thus, according to the present invention, the metal exposure of a area having an optional shape can be measured.

Referring to FIGS. 3 and 4 illustrating the systematic arrangement of the apparatus for use in carrying out the method of the present invention, this apparatus comprises a supporting member 11 for supporting a sample 1 to be measured and a contact electrode 10 in the electrically conductive state, an electrode supporting mechanism 12 including a measuring electrode 6 and an electrolytic solution holding member 8 arranged on the tip of said electrode, a driving mechanism 13 (see FIG. 4) for relatively moving the supporting member 11 and the electrode supporting mechanism 12 in the above-mentioned contact state, a drive control mechanism 14 for controlling the driving of the driving mechanism 13 according to predetermined parts to be measured, an interface zone 15 for applying a voltage between the contact electrode 10 and the measuring electrode 6, measuring a leak current at every predetermined pitch of the relative movement and performing analog-digital conversion of the measured current value, and a data processing zone 16 for performing statistical processing of the digital-converted data and displaying or recording the obtained data. This data processing zone 16 comprises a computer 17, a keyboard 18, a cathode ray tube (CRT) and a printer 20.

Referring to FIG. 4 illustrating the supporting member 11, electrode supporting mechanism 12 and driving mechanism 13, which are used for measuring the metal exposure of a seam covering of a welded seam can, the supporting member (supporting stand) 11 is vertically movably mounted on a machine frame 21 through a slide shaft 22 extending in the vertical direction. The supporting stand 11 is contacted with a cam plate 24 driven by a motor 23 so that the supporting stand 11 can be located at a position of an optional height by turning the cam plate 24. A holder 25 is disposed on the supporting stand 11 to support a sample can 1 in the state laid in a certain direction, that is, in the left-right direction in FIG. 4. On one end of the holder 25, that is, on the left end of the holder 25 in FIG. 4, there is disposed the contact electrode 10 contacted with the end of the flange of the sample can 1 and electrically connected thereto. A slidable stopper 26 for fixing the sample can body 1 is arranged on the other end of the holder 25, that is, on the right end of the holder 25 in FIG. 4.

The holder 25 is capable of holding a can body having an optional diameter and an optional height, and as shown in the sectional view of FIG. 5, the holder 25 has two confronting tapered areas 27 opened upward. The stopper 26 can be optionally adjusted according to the height of the can body, and the stopper 26 can press the can body 1 to the contact electrode 10 under a certain load. In the supporting stand 11, a small tank 28 for containing therein the electrolytic solution for the measurement is disposed on the end opposite to the end where the holder 25 is arranged. In the present invention, a single holder 25 may be arranged on the supporting stand 11, or a plurality of holders may be arranged so that a plurality of can bodies can be measured simultaneously and concurrently. In the embodiment illustrated in the accompanying drawings, five holders are arranged and five samples are simultaneously measured.

The electrode supporting mechanism 12 comprises a stand 29, a sliding shaft 30 which is supported on the stand 29 so that it can move in the horizontal direction, a measuring electrode 6 fixed to the sliding shaft 30 through a bracket 31, and an electrolytic solution holding member 8 mounted on the tip of the measuring electrode 6, that is, the lower end of the measuring electrode 6. A driving mechanism 13 (indicated by a one-dot chain line) for driving the sliding shaft 30 in the horizontal direction is built in the stand 29. The measuring electrode 6 is arranged so that certain displacement in the vertical direction is allowed. Accordingly, under the measurement conditions the measuring electrode 6 is brought into contact with the measurement part of the sample can body 1 by the gravity, and even if convexities and concavities extending the vertical direction are present at the measurement part, the relative movement can be performed between the electrode 6 and the can body 1 in such a manner that the electrode 6 can precisely trace these convexities and concavities.

A porous member composed of a fiber or resin capable of holding the electrolytic solution is ordinarily used as the electrolytic solution holding member 8. Of course, it is indispensable that the holding member 8 should exude the electrolytic solution to the resin covering surface of the sample can body by the contact pressure so that the resin covering surface is wetted with the electrolytic solution. For this purpose, there are advantageously used woven or nonwoven fabrics of natural or regenerated fibers such as cotton fibers or regenerated cellulose fibers, synthetic fibers such as polyvinyl alcohol fibers, acrylic fibers, nylon fibers and polyester fibers or mixtures thereof, open-cell foamed members of polyurethane or other synthetic resin, porous glass members and ceramic members. In general, a fibrous material in which the critical water retention quantity per unit weight of the material (the largest quantity of water that can be retained without dropping of water) is 0.1 to 100 g/g, especially 0.5 to 50 g/g, is preferably used. In view of the water-retaining property and strength, a gauze of a water-absorbing fiber such as cotton or a porous woven fabric of silk or gossamer is satisfactory as the holding member 8. The shape of the holding member 8 is not particularly critical, so far as the holding member 8 can envelope the tip of the electrode therein at the measurement. For example, in case of the above-mentioned porous woven fabric, the holding member 8 is wound on the tip of the electrode or used in the form of a bag capped on the electrode.

The sectional shape and size of the measuring electrode 6 are not particularly critical but optional. For example, the measuring electrode may be in the form of a column or square pillar. However, it is generally preferred that the length of the electrode in the advancing direction be 0.1 to 10 mm. The material of the electrode is not particularly critical, so far as the electrode is composed of a corrosion-resistant electroconductive material such as stainless steel, nickel, platinum or carbon rod.

A solution having an electroconductivity of 0.1 to 400 m-mho/cm, especially 0.5 to 200 m-mho/cm, in which the contact angel to the resin covering of a sample to be measured is smaller than 90°, especially smaller than 85°, is preferably used as the electrolytic solution. The solution consists essentially of an aqueous solution containing a water-soluble salt such as sodium chloride, potassium chloride, sodium sulfate, potassium sulfate or sodium nitrate, an inorganic or organic acid or an electrolyte such as an inorganic or organic base at a concentration of 0.05 to 70% by weight. In order to improve the wettability to the organic resin covering and the permeability to the metal-exposed part through the defect of the covering, a surface active agent such as an anionic surface active agent, a non-ionic surface active agent or an amphoteric surface active agent, an alcohol such as methanol, ethanol or isopropanol, a ketone such as acetone or methylethyl ketone or other water-miscible organic solvent such as an ether may be incorporated into the electrolytic solution.

Before the measurement, basic data of various sample cans, such as the can diameter, the can height, the can kind and the use, are recorded in the computer 17. By the keyboard 18, the kind and use of the can to be measured are put in, and the sample can 1 is attached to the holder 25 so that the covered weld seam 2 is located at the lowermost position. Since the kind of the electrolytic solution to be used for the measurement is designated by putting-in of the above-mentioned data, the designated electrolytic solution is filled in the tank 28.

Then, the start of the measurement is put in by the keyboard 18. The respective mechanisms are driven in the following order according to instructions from the computer 17. At first, the motor 23 and, in turn, the cam plate 24 are driven, and the supporting stand 11 rises and the electrolytic solution holding member 8 on the tip of the electrode 6 is immersed in the electrolytic solution 7 contained in the tank 28, and a predetermined amount of the electrolytic solution is retained in the holding member 8. Then, the motor 23 and, in turn, the cam plate 24 are driven, and the supporting stand 11 drops and stops at a predetermined position. The driving mechanism 13 in the electrode supporting mechanism is driven, and the slide shaft 30 and, in turn, the measuring electrode 6 begin preliminary movement (movement to the left in the drawings) and the electrode 6 is inserted into the can and stopped at the position for initiating the measurement. Then, the motor 23 and cam plate 24 for the supporting stand 11 are driven to elevate the supporting stand 11 and stop the supporting stand 11 at the position where the measuring electrode 6 falls in contact with the compensating resin covering layer 5 (see FIG. 1) of the sample can body 1 through the electrolytic solution.

From this position, the driving mechanism 13 is driven again, and the slide shaft 30 and, in turn, the measuring electrode 6 are moved for the measurement (moved to the right in the drawings). At this movement for the measurement, a certain voltage is applied between the measuring electrode 6 and the contact electrode 10 at every predetermined pitch through the interface zone 15 according to instructions from the computer 17, and a leak current generated between the measuring electrode 6 and the contact electrode 10 is analog-digital-converted in the interface zone 15 and the digital measurement value is put in the computer 17.

The leak current values put in the computer 17 are recorded for respective pitches, that is, respective measurement positions, discriminately, and the statistical processing is carried out for determining the distribution of the leak current values, the mean value and the maximum and minimum values, comparing the leak current values with the preset allowable range and judging acceptance or rejection is performed. The result is displayed as a table or graph by CRT 19 or is put out as a print by the printer 20.

The range of the scanning measurement movement of the measuring electrode 6 is set according to the can height corresponding to the kind of the can to be measured, and on termination of the scanning measurement movement, the motor 23 and, in turn, the cam plate 24 are driven and the supporting stand 11 is dropped to the predetermined position. The slide shaft 30 is further moved to the right and is stopped when the measuring electrode 6 arrives at the position above the tank 28.

The pitch width for the measurement of the leak current depends on the size of the electrode 6, but it is preferred that the measurement pitch width be 0.1 to 10 mm, especially 1 to 5 mm. In view of the measurement precision, it is preferred that the relative moving speed of the measuring electrode 6 be lower than 300 mm/sec, especially 10 to 100 mm/sec. It is sufficient if the voltage applied between the two electrodes is small, because the distance between the measuring electrode and the metal-exposed part is small. the voltage is generally 0.1 to 30 volts and preferably 0.5 to 15 volts. A direct current voltage is preferably used as the measuring voltage. The leak current is detected as the drop of the voltage by the resistance and the drop of the voltage is converted and read in as the data. The time required for the measurement of the leak current is so short as 1 to 25 microseconds, and a large number of leak currents can be simultaneously measured.

According to the above-mentioned measuring apparatus, the metal exposure of a straight seam on the inner surface of the can can be measured. However, the present invention can be applied to the measurement of the metal exposure of a resin covering at any area of a constituent member of a metal container.

For example, a bottle-shaped metal container formed by fitting a funnel-shaped lid obtained by draw-forming a coated metal plate into a coated bottomed body prepared by drawing and ironing to form a circumferential seam, as disclosed in Japanese Patent Application Laid-Open Specification No. 47338/76, is known. This lid has caused at these stepped parts because of severe processing.

According to the present invention, even the metal exposure of this circumferential stepped part can be measured. Referring to FIGS. 6 and 7 illustrating the apparatus to be used for this measurement, this lid 40 comprises a tapered shoulder 41 prepared by drawing a coated metal plate and a small-diameter cylindrical neck 42. A plurality of circumferential stepped parts 43a and 43b are formed in the midway of the tapered shoulder 41, and a broad circumferential stepped part 44 acting as the fitting part to a body (not shown) is formed on the outer side of the tapered shoulder 41.

Roughly speaking, also this measuring apparatus comprises a sample supporting member 11, an electrode supporting mechanism 12 and a driving mechanism 13. In the present embodiment, the sample supporting member 11 is a holder and is mounted on a stand comprising a vertical area 50 and a horizontal area 51. More specifically, a rotation shaft 52 is attached to the vertical area 50 and the holder 11 for the lid 40 is dismountably attached to the shaft 52. The holder 11 has a hollow cup-like shape and the lid 40 can be secured and contained in the interior 53 of the holder 11. A contact electrode 10 conductive to the metal substrate of the lid 40 is arranged on the open end of the holder 11. A small tank 28 for containing therein an electrolytic solution 7 for the measurement is arranged on one end of the horizontal area 51.

The electrode supporting mechanism 12 comprises a vertical slide shaft 54, a horizontal rod 55 attached orthogonally to the vertical slide shaft 54 through a supporting area 55', a vertically driving motor and linear head 56 for driving and moving the vertical slide shaft 54 in the vertical direction, a horizontal direction slide mechanism 57 for supporting the linear head 56 movably in the horizontal direction, and a horizontally driving motor and linear head 58 for driving the vertical linear head 56 in the horizontal direction through the horizontal direction slide mechanism 57. A pair of a downward measuring electrode 6 and an electrolytic solution holding member 8 are arranged on the top end of the horizontal rod 55. Accordingly, the measuring electrode 6 is vertically moved by driving of the vertically driving linear head 56 and the measuring electrode 6 is horizontally moved by driving of the horizontally driving linear head 58. Incidentally, the horizontal rod 55 is attached to the supporting area 55' of the vertical slide shaft 54 so that certain swinging movement is allowed and the measuring electrode 6 is contacted with the measurement part of the sample lid 40 under a certain contact pressure by the gravity of the horizontal rod 55.

The driving mechanism 13 for relatively moving the sample supporting member 11 and the measuring electrode 6 comprises a pulse motor or a servo motor in the present embodiment, and the driving power of this motor is transmitted to the rotation of shaft 52 supporting the holder 11 through a pulley 59, an endless belt 60 and a pulley 61.

Also in the measuring apparatus shown in FIGS. 6 and 7, the driving control and the data processing are carried out in the same manner as in the system shown in FIG. 3. Each of the driving motors is a pulse motor, and the position can be judged by the driving pulse member. Of course, a servo motor can be used instead of the pulse motor and the position can be controlled by the servo mechanism.

At first, the kind, use and other data of the lid to be measured are put in by the keyboard 58 in FIG. 3 and the sample lid 40 is attached to the predetermined lid holder 11. The predetermined electrolytic solution 7 is filled in the tank 28, and instructions for starting the measurement are given by the keyboard 18.

Referring to FIG. 6, the vertically driving motor and linear head 56 drives the measuring electrode 6 to elevate the measuring electrode 6 in the state where the electrolytic solution holding member 8 arranged on the tip of the measuring electrode 6 holds the electrolytic solution. When the measuring electrode 6 arrives at the predetermined position, the vertically driving motor 56 is stopped and the horizontally driving motor and linear head 58 is driven to horizontally move the measuring electrode 6 (to the left in the drawings) so that the measuring electrode 6 is inserted into the lid 40. When the measuring electrode 6 arrives at the first measurement position, that is, the position corresponding to the circumferential stepped part 43a, the horizontally driving motor 58 is stopped and the vertically driving motor and linear head 56 is driven to drop the measuring electrode 6. Then, the vertically driving motor 56 is stopped and the measuring electrode 6 is brought into contact with the circumferential stepped part 43a through the electrolytic solution. In this state, the driving mechanism 13 is driven to make one rotation in the lid holder 11 and measure the leak current at respective certain pitches discriminately over one circumference of the inner surface of the circumferential stepped part 43a.

After the measurement, the horizontally driven motor and linear head 56 is driven to move the measuring electrode 6 to the right, and when the measuring electrode 6 arrives at the position corresponding to the next circumferential stepped part 43b, the vertically driving motor and linear head 56 is driven and dropped and the measuring electrode 6 is brought into contact with the circumferential stepped part 43b. In the same manner as described above, the leak current is measured at respective certain pitches discriminately over one circumference of the stepped part 43b. This operation is conducted repeatedly to the final stepped part 44.

The measuring method of the present invention can be applied to the metal exposure of a riveted or score area in an easy-open lid having a coated inner surface.

Figure 8:
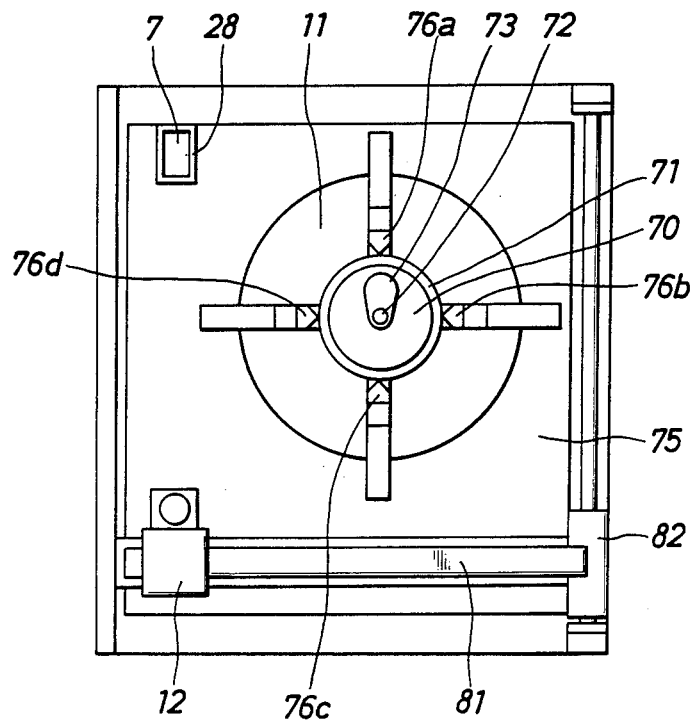
FIG. 8 is a top view showing a main part of the apparatus used for measuring the metal exposure in an easy-open lid.
Figure 9:
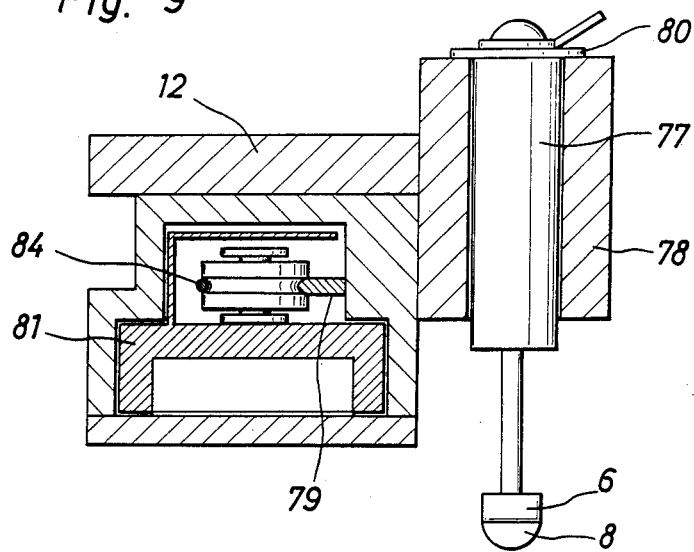
FIG. 9 is an enlarged sectional view of an electrode supporting mechanism in the apparatus shown in FIG. 8.
Figure 10:
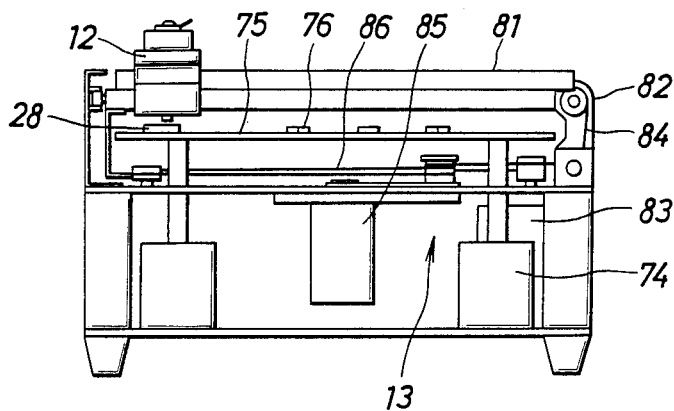
FIG. 10 is a side view of the apparatus shown in FIG. 8.

Referring to FIG. 8 illustrating the apparatus to be used for this measurement, an easy-open lid 70 to be measured comprises a sealing groove 71 on the periphery and a riveted area 72 and a scored area 73 at the center. In principle, the measuring apparatus comprises a lid supporting member 11, an electrode supporting mechanism 12 and a driving mechanism 13, as shown in FIGS. 8, 9 and 10.

The lid supporting member 11 comprises a supporting stand 75 vertically movably attached to a machine frame through a vertically driving cylinder 74, and a cruciform lid pressing contact electrode 76 attached to the supporting stand 75. Pressing pieces 76a, 76b, 76c and 76d of the lid pressing contact electrode 76 are slidable inwardly and outwardly with respect to the diameter of the lid 70, and they are always urged inwardly with respect to the diameter by a force of a spring (not shown). Thus, electric conduction is attained between the contact electrode and the lid through the peripheral edge of the lid. The lid 70 is attached to the supporting member 11 so that the inner surface (resin-covered surface) is located above.

The electrode supporting mechanism 12 comprises a vertically sliding shaft 77 supporting the measuring electrode 6, a holder 78 holding the sliding shaft 77 slidably, and an attachment area 79 for attaching the holder 78 to a driving mechanism described hereinafter. A stopper 80 is mounted on the top end of the sliding shaft 77, so that the sliding shaft 77 contacts the lid to be measured under a certain gravity and moves in the vertical direction according to convexities and concavities on the surface to be measured.

The driving mechanism 13 comprises a Y-axis slide 81 supporting the electrode supporting mechanism 12 slidably in the Y-axis direction and an X-axis slide 82 supporting the Y-axis slide 81 slidably in the X-axis direction. For driving the electrode supporting mechanism 12 along the Y-axis slide 81, a Y-axis driving motor 83 and a Y-axis driving wire 84 are disposed. Furthermore, for driving the Y-axis slide 81 along the X-axis slide 82, an X-axis driving motor 85 and an X-axis driving wire 86 are disposed. The X-axis and Y-axis driving mechanisms are known as the driving mechanism for a so-called X-Y plotter. For example, X-Y driving is accomplished by connecting respective slide areas through wires by a servo mechanism (by a DC motor and a potentiometer). The precision of the movement position is in an order of about 0.1 mm.

A tank 28 containing an electrolytic solution 7 therein is disposed in the end area of the supporting stand 75.

Prior to the measurement, with respect to various easy-open lids, basic data such as the lid diameter, the shape and position of the score, the shape and position of the rivet and the inner surface covering material are stored in the computer 17. The kind, use and other data of the lid to be measured are put in by the keyboard 18, and the lid 70 is set at a predetermined position. A predetermined electrolytic solution 7 is filled in the tank 28, and an order of the start of the measurement is put in through the keyboard 18.

At the start of the measurement, the supporting stand 75 is located at the drop position, an electric power corresponding to predetermined X-Y coordinate values is put in the X-Y driving systems 83 and 85, and the measuring electrode 6 is moved to the position above the electrolytic solution tank 28. The vertically driving cylinder 74 is driven and elevated, and after the electrolytic solution holding member 8 on the tip of the electrode has been impregnated with a predetermined quantity of the electrolytic solution, the supporting stand 75 is dropped to the determined position again.

Then, an electric power corresponding to X-Y coordinate values of the measurement-initiating position of the scored area 73 or riveted area 72 is put in the X-Y driving systems, and the measuring electrode 6 arrives at the position above the set position of the lid 70. At this point, the vertically driving cylinder 74 is driven and elevated, and the measuring electrode 6 is brought in contact with the inner surface of the lid through the electrolytic solution. The measuring electrode 6 is horizontally driven in the X-Y direction precisely along the pattern of the scored area or riveted area stored in the computer 17. The leak current is measured at every constant pitch over the fabricated area, and the measured values are subjected to statistical processing by the computer.

In the foregoing illustration, the leak current is measured at every constant pitch only over the scored or riveted area of the easy-open lid. Of course, there may be adopted a method in which the electrode 6 is moved and scanned over the entire inner surface of the lid and the leak current is measured at respective constant pitches over the entired inner surface including the scored area and riveted area.

As is apparent from the foregoing description, according to the present invention, with respect to a covered metal containerhaving an optional shape or a constituent member thereof, the degree of the metal exposure can be simply measured as a leak current value at respective parts discriminately, and the present invention is very effective for controlling the quality of metal containers and controlling the preparation process thereof.

The present invention will now be described in detail with reference to the following examples that by no means limit the scope of the invention.

EXAMPLE 1

An epoxy-phenolic resin lacquer was coated and baked in a thickness of 7 m on the inner surface of a large tinplate sheet having a deposition of tin amount of 2.8 g/m² and a thickness of 0.20 mm, and the outer surface was printed. The large sheet was cut into a blank of 136.52 mm×165.90 mm by a slitter and the blank was welded by a welder to form a cylindrical can having a nominal diameter of 202 and a weight of 250 g.

The inner surface side seam area was repaired with a repairing lacquer shown in Table 1, and the repairing lacquer was dried and cured under conditions shown in Table 1.

The side seam-repaired cylindrical can was subjected to multi-bead processing and necking processing according to customary procedures, and with respect to samples indicated by mark "D" in Table 1, the inner surface was spray-coated and the coating was dried under customary conditions.

In order to confirm the correction state of the inner surface side seam area of the can body, the metal exposure was measured by a 1% NaCl electrolytic solution having an anionic surface active agent incorporated therein in the apparatus shown in FIGS. 3 through 5. With respect to each sample, 100 cans were tested. The results obtained are shown in Table 1. Separately, 100 cans prepared under the same conditions as described above were filled with orange juice and stored at 37° C. for 6 months, and the amount of iron dissolved in the content was measured.

The results obtained are shown in Table 1.

TABLE 1

| | ISS (correction of inner surface side seam) | | | | Metal Exposure (mA) | | | Orange Juice Amount of Dissolved iron (37° C. 6 months) |
|---|---|---|---|---|---|---|---|---|
| | Coating Manner | Material | Average Thickness | Baking Conditions | Σ | Max | Remarks | |
| A | spraying | modified alkyd-amide | 8 μm | 250° C. 3 seconds | 50 | 5 | extreme metal exposure in bead-processed portion | 17 ppm |
| B | spraying | epoxyphenol-polyamide | 16 μm | 250° C. 3 seconds | 3 | 0.8 | extreme metal exposure in bead-processed portion | 10 ppm |
| C | spraying | phenol-modified epoxy ester | 32 μm | 210° C. 100 seconds | 0.1 | 0.05 | 2 to 3 metal-exposed parts | 2 ppm |
| D | body spraying after spraying | epoxyphenol-polyamide | 16 μm | 250° C. 3 seconds | 0 | 0 | | 0 ppm |

Note
Can: 250 g (tinplate #25, welded can)
Welding machine: FBB540
Electrolytic solution: 1% NaCl, surface active agent added
Pitch of measurement of metal exposure: once/1 mm
Electroconductivity: 15 m-mho/cm
Electrode: square pillar (1 mm×1 mm), stainless steel
Contact angle: 40°
Applied voltage: 5 volts
Scanning speed: 30 mm/sec
Holding member: cotton gauze

EXAMPLE 2

An epoxy-phenolic resin lacquer was coated and baked in a thickness of 7 μm on the inner surface of a nickel-tin covered steel plate having a thickness of 0.21 mm, and the outer surface was printed. The plate was cut into a blank of 136.52 mm×165.90 mm by a slitter and the blank was welded by a welding machine to prepare a cylindrical can having a nominal diameter of 202 and a weight of 250 g.

The side seam was repaired with a repairing lacquer material shown in Table 2 in a manner shown in Table 2 and the repairing lacquer was cured or bonded under conditions shown in Table 2.

The side seam-repaired cylindrical can was subjected to necking processing according to customary procedures, and in order to confirm the repair state of the inner surface side seam area of the barrel, the metal exposure was measured by a mixed electrolytic solution containing 1.5% of $NaCO_3$ and 1% of $NaHCO_3$, in which a non-ionic surface active agent had been incorporated, in the apparatus shown in FIGS. 3 through 5 (the electrode and holding member were the same as in Example 1). With respect to each sample, 100 cans were tested. The results obtained are shown in Table 2.

Separately, 100 cans prepared under the same conditions as described above were packed with a coffee drink and stored at room temperature for 6 months, and the amount of iron dissolved in the content was measured. The results obtained are shown in Table 2.

diameter of 202 and a weight of 250 g. Incidentally, the side seam inside cut edge was covered with the nylon film.

The cylindrical can was subjected to necking processing according to customary procedures. Then, the metal exposure of the inner surface side seam area of the can barrel was measured by an electrolytic solution containing 1% of strontium chloride in the apparatus shown in FIGS. 3 through 5. The test was conducted on 100 cans. The results obtained are shown in Table 3. Separately, 100 cans were prepared under the same conditions as described above, packed with a coffee drink and stored at room temperature for 6 months. The amount of iron dissolved in the content was measured. The obtained results are shown in Table 3.

In all of the cans where the metal exposure was measured, the leak current was zero.

Incidentally, dissolution of iron was not observed.

TABLE 3

Adhesive material
Adhesive: nylon
Average thickness: 40 μm
Bonding temperature: 240 to 260° C.
Metal Exposure (mA)
Σ: 0
Max: 0
Remarks:
Coffee Drink
Amount of dissolved iron 0 ppm (room temperature,

TABLE 2

| ISS (correction of inner surface side seam) | | | | Metal Exposure (mA) | | | Coffee Drink Amount of Dissolved Iron (room temperature, 6 months) |
|---|---|---|---|---|---|---|---|
| Coating Manner | Material | Average Thickness | Baking Conditions | Σ | Max | Remarks | |
| spraying | thermosetting vinyl | 16 μm | 175° C. 4 minutes | 3.5 | 0.13 | extreme metal exposure at necked part | 1.2 ppm |
| spraying | epoxyphenol | 16 μm | 250° C. 100 seconds | 4 | 0.16 | extreme metal exposure at necked part | 1.6 ppm |
| roll coating | vinyl organosol | 30 μm | 250° C. 3 seconds | 3 | 0.20 | extreme metal exposure at necked part | 1.0 ppm |
| powder | polyester | 90 μm | 270° C. 9 seconds | 0.2 | 0.1 | reaction sometimes occurred at necked part | 0.1 ppm |
| adhesive tape | polyester | 80 μm | bonding 200 to 280° C. | 0 | 0 | | 0.1 ppm |

Note
Can: 250 g (Ni-Sn covered steel plate, welded can)
Welding machine: FBB540
Electrolytic solution: 1.5% $Na_2CO_3$+1% $NaHCO_3$+surface active agent
Pitch of measurement of metal exposure: once/1 mm
Electroconductivity: 20 m-mho/cm
Contact angle: 35°

EXAMPLE 3

A primer was coated and baked in a thickness of 3 μm on both the surfaces of a large TFS sheet having a thickness of 0.21 mm, and an epoxy-phenolic lacquer was further coated and baked in a thickness of 5 μm on the inner surface except a bonding margin while the outer surface was printed except a bonding margin. The large sheet was cut into a blank of 136.52 mm×170.40 mm with an appropriate bonding margin by a slitter. The blank was bonded with a nylon film by a body maker to obtain a cylindrical can having a nominal 6 months):
Note
Can: 250 g (TFS, bonded can)
Pitch of measurement of metal exposure: once/3 mm
Electrolytic solution: 1% strontium chloride
Electrodes: square pillar (3 mm×3 mm), stainless steel
Electronconductivity: 7 m-mho/cm
Contact angle: 70°
Holding member: open-cell foamed polyurethane

EXAMPLE 4

An epoxy-phenolic resin lacquer was coated in a thickness of 7 μm on the inner surface of a nickel-tin covered steel plate having a thickness of 0.22 mm, and the outer surface was printed. The plate was cut into a blank of 185.13 mm×99.25 mm by a slitter and welded by a welding machine to form a cylindrical can. Then, the side seam was repaired with a repairing lacquer shown in Table 4, and the repairing lacquer was dried and cured under conditions shown in Table 4. Then, the cylindrical can was subjected to bulging processing to form a deformed cylindrical can having a weight of 250 g. Then, a thermosetting vinyl resin was spray-coated and baked on the inner surface of the deformed cylindrical can. In order to confirm the repair state of the inner surface side seam of the can barrel, the metal exposure was measured by using an electrolytic solution containing 1% of hydrochloric acid in the apparatus shown in FIGS. 3 through 5 (the electrode and holding member were the same as those used in Example 1). The results of the measurement conducted on 100 cans are shown in Table 4.

Separately, 100 cans prepared under the same conditions as described above were packed with a coffee drink and stored at room temperature for 6 months, and the amount of iron dissolved in the content was measured. The obtained results are sown in Table 4.

The metal exposure occurred concentratedly in the bulged area, and the test was effective for clarifying this fact.

TABLE 4

| ISS (correction of inner surface side seam) | | | Metal Exposure (mA) | | | Coffee Drink Amount of Dissolved Iron (room temperature, 6 months) |
|---|---|---|---|---|---|---|
| Coating Manner | Material | Average Thickness | Baking Conditions | Σ | Max | Remarks |
| spraying | epoxyphenol-polyamide | 26 μm | 250° C. 3 seconds | 1 | 0.03 | extreme metal exposure in bulged portion | 0.2 ppm |

Note
Can: 250 g inner surface-spray coated can (Ni-Sn covered steel plate, deformed welded can)
  Welding machine : FBB500
  Electrolytic solution: 1% hydrochloric acid
  Pitch of metal exposure emasurement: once/1 mm
  Electroconductivity: 95 m-mho/cm
  Contact angle: 70°

EXAMPLE 5

In Run A, a full-open end having a nominal diameter of 307 was prepared by coating and baking a lacquer on the outer surface of a large aluminum sheet having a thickness of 0.3 mm, laminating a PET film on the inner surface of the aluminum sheet and subjecting the aluminum sheet to an ordinary forming operation.

In Run B, a full-open end having a nominal diameter of 307 was prepared by coating and baking a lacquer on the outer surface of a large aluminum sheet having a thickness of 0.3 mm, coating a vinyl organosol lacquer in a thickness of 4 μm on the inner surface and subjecting the aluminum sheet to an ordinary forming operation, and the inner surface of the lid was spray-corrected with a polyester-epoxy lacquer.

The metal exposure of the scored and riveted area of these lids was measured by an electrolytic solution containing 10% NaCl in the apparatus shown in FIGS. 8 through 10. With respect to each sample, 100 lids were tested. The results obtained are shown in Table 5.

Tinplate welded cans (Tuna #2 can) seamed with the two lids prepared under the same conditions as described above were packed with tuna brine and stored at 37° C. for 6 months. Formation of pitting was checked. The obtained results are shown in Table 5.

TABLE 5

| | | Inner Surface | | | | | Tuna Brine Perforating Ratio (37° C., 6 months) |
|---|---|---|---|---|---|---|---|
| Run | Coating Material | Average Thickness | Baking Conditions | Metal Exposure (mA) | | | |
| | | | | Σ | Max | Remarks | |
| A | PET film laminated | 25 μm | | 0.05 | 0.02 | | 0% |
| B | polyester-epoxy/vinyl organosol | 8/4 μm | 250° C., 4 minutes/250° C., 10 minutes | 0.5 | 0.1 | metal exposure at second portion | 0.5% |

Note
Lid: 307-diameter full-open end (aluminum)
Electrode: radius 1 mm semi-columnar stainless steel electrode
Electrolytic solution: 10% NaCl
Holding member: water-absorbing acrylic fiber gauze
Electroconductivity: 100 m-mho/cm
Contact angle: 80°
Voltage: 3 volts
Measurement pitch: once/1 mm

EXAMPLE 6

The metal exposure of the repaired inner surface of side seam of the barrel of an ordinary welded can for a coffee drink having a nominal diameter of 202 and a weight of 250 g was measured by using mercury or an electrolytic solution shown in Table 6 in the apparatus shown in FIGS. 3 through 5. With respect to each sample, 100 cans were tested. The results obtained are shown in Table 6. Incidentally, the same electrode and holding member as described in Example 1 were used except the case where mercury was used. When mercury was used, a pipe electrode having a diameter of 1 mm was used.

Separately, the can was packed with a coffee drink and stored at room temperature for 6 months, and the amount of iron dissolved in the content was measured. The results obtained are shown in Table 6.

When mercury was used as the electrolyte, since the wettability to the compensating material was poor, fine metal exposure could not be detected.

Furthermore, when an electrolytic solution having a very low electroconductivity was used, the leak current was very small and proper evaluation was difficult. When an electrolytic solution having a very high electroconductivity was used, breaking of the repairing material was occurred and the leak current value measured was not corresponding to the metal-exposed area originally existed in the side seam of the can.

TABLE 6

| | Contact Angle θ (°) | Electroconductivity X (m-mho/cm) | ERV (mA) Σi | ERV (mA) Maxi | Amount of Iron Dissolved in Coffee (room temperature, 6 months) |
|---|---|---|---|---|---|
| mercury | 140 | — | 0 | 0 | 1.0 to 1.4 ppm |
| 0.05% NaCl | 78 | 0.05 | 0.05 | 0.01 | " |
| 1% NaCl | 83 | 15 | 4 | 1.0 | " |
| 30% HCl | 75 | 662 | 500 | 25 | " |

EXAMPLE 7

The inner surface of a bottomed can barrel prepared by drawing-ironing of an aluminum sheet having a thickness of 0.44 mm was coated and baked and the outer surface was printed. Furthermore, an aluminum sheet having a thickness of 0.25 mm and having both the inner and outer surfaces coated was drawn into a funnel-shaped lid having a multi-stepped fabricated area.

In order to confirm the coating-damaged state of the stepped area of the lid, the metal exposure in several lots of lids was measured by using an electrolytic solution containing 10% of NaCl in the apparatus shown in FIGS. 6 and 7 (radius 2 mm columnar stainless steel electrode was used as the measuring electrode).

These several lots of lids were fitted to inner surface-coated bottomed can barrels through an adhesive. The formed cans were packed with beer and stored at room temperature for 6 months, and the quality of the content was examined.

As the result, it was found that in the lot where the leak current at each metal-exposed part was smaller than 1 mA and the statistical value was smaller than 5 mA, there was no problem of the quality, but in the lot where the statistical value of the leak current was larger than 50 mA, beer became cloudy.

From the results of the foregoing results, it is seen that according to the measuring method of the present invention, the metal exposure at each part can be measured as a leak current value, the statistical processing for obtaining the sum or the maximum value can be easily performed, and a definite corelation is established between the measured leak current value and the dissolution or corrosion of the metal in actual cans.

What is claimed is:

1. A method for measuring the metal exposure in a resin covering the area of a metal container or a constituent member thereof, which comprises:
   (i) preparing an electrolytic aqueous solution having an electroconductivity of 0.1 to 400 m-mho/cm and a contact angle of less than 90° on a resin covering to be measured,
   (ii) immersing and withdrawing a holding member mounted on a tip of a measuring electrode in and from the electrolytic solution to thereby retain a predetermined amount of the electrolytic solution in the holding member,
   (iii) contacting the resin covering area of the metal container or the constituting member thereof with the measuring electrode through the electrolytic solution,
   (iv) relatively moving the resin covering area and the measuring electrode in a certain direction while always holding the electrolytic solution between the measuring electrode and the resin covering area,
   (v) applying a voltage of 0.1 to 30 volts between the measuring electrode and the metal substrate of the metal container or the constituent member thereof, and
   (vi) intermittently measuring a leak current between the measuring electrode and the metal substrate of the metal container or the constituent member thereof at every pitch of 0.1 to 10 mm to thereby detect metal exposure of the resin covering area as leak current at respective parts discriminately.

2. A measuring method according to claim 1, wherein the holding member comprises a porous fibrous material in which the critical water retention quantity per unit weight of the material is 0.1 to 100 g/g.

3. A measuring method according to claim 1, wherein the holding member comprises a porous woven fabric which is wound on the tip of the electrode or is a bag capped on the electrode.

4. A measuring method according to claim 1, wherein the length of the electrode in the advancing direction is 0.1 to 10 mm.

5. A measuring method according to claim 1, wherein the relative moving speed of the measuring electrode is 10 to 100 mm/sec.

6. A method of measuring the metal exposure in a resin covering area of a metal container or a constituent member thereof, which comprises:
   (i) preparing an electrolytic aqueous solution having an electroconductivity of 0.1 to 400 m-mho/cm and a contact angle of less than 90° C. on a resin covering to be measured,
   (ii) immersing and withdrawing a holding member mounted on a tip of a measuring electrode in and from the electrolytic solution to thereby retain a predetermined amount of the electrolytic solution in the holding member.
   (iii) contacting the resin covering area of the metal container or the constituting member thereof with the measuring electrode through the electrolytic solution,
   (iv) relatively moving the resin covering area and the measuring electrode in a certain direction while always holding the electrolytic solution between the measuring electrode and the resin covering area,
   (v) applying a voltage of 0.1 to 30 volts between the measuring electrode and the metal substrate of the metal container or the constituent member thereof.
   (vi) intermittently measuring a leak current between the measuring electrode and the metal substrate of the metal container or the constituent member thereof at every pitch of 0.1 to 10 mm,
   (vii) subjecting the leak current value measured at every pitch to analog-digital conversion, and
   (viii) subjecting the obtained digital value to statistical processing by means of a computer.

7. A method for measuring according to claim 6, wherein the statistical processing is carried out for determining the distribution of the leak current value, the mean value and the maximum and minimum values, comparing the leak current value with an allowable range and judging acceptance or rejection.

8. An apparatus for measuring metal exposure in a resin covering area of a metal container or a constituent member thereof, which comprises:
- a measuring electrode;
- a contact electrode;
- a tank containing an electrolytic solution therein;
- a holding member for retaining the electrolytic solution, which is composed of a porous material and mounted on the tip of said measuring electrode;
- a supporting member for supporting the metal container or the constituent member thereof, which has the resin covering area, in a state electrically conductive to the contact electrode;
- an electrode supporting member for supporting said measuring electrode, which is arranged so that the resin covering area of the metal container or the constituent member thereof is contacted with the measuring electrode through the electrolytic solution;
- a driving mechanism for the supporting member and the electrode supporting member, which is disposed to
  - (i) immerse and withdraw the holding member in and from the electrolytic solution to retain a predetermined amount of the electrolytic solution in the holding member,
  - (ii) move the measuring electrode to a position for initiating the measurement, and
  - (iii) relatively move said supporting member and said electrode supporting member while keeping said electrical contact state;
- a computer for controlling the driving mechanism and for controlling measurement;
- an interface means of a computer for applying a voltage between the contact electrode and the measuring electrode, for measuring a leak current between said electrode at every predetermined pitch of the relative movement and for performing analog-digital conversion of the measured current value; and
- a data processing means of a computer for performing statistical processing of the measured current value as digital data and displaying and recording the obtained data.

* * * * *